(12) United States Patent
Blankenbecler

(10) Patent No.: US 11,684,802 B2
(45) Date of Patent: *Jun. 27, 2023

(54) REDUCING DAMAGE FROM RADIATION THERAPY AND INCREASING CANCER KILL RATES BY INTERWEAVING OF LOW AND HIGH DOSE SESSIONS

(71) Applicant: Radiation Barrier LLC, Henderson, NV (US)

(72) Inventor: Richard Blankenbecler, Henderson, NV (US)

(73) Assignee: Radiation Barrier LLC, Henderson, NV (US)

( * ) Notice: Subject to any disclaimer, the term of this patent is extended or adjusted under 35 U.S.C. 154(b) by 243 days.

This patent is subject to a terminal disclaimer.

(21) Appl. No.: 16/474,863

(22) PCT Filed: Jan. 2, 2018

(86) PCT No.: PCT/US2018/012097
§ 371 (c)(1),
(2) Date: Jun. 28, 2019

(87) PCT Pub. No.: WO2018/126277
PCT Pub. Date: Jul. 5, 2018

(65) Prior Publication Data
US 2019/0329069 A1    Oct. 31, 2019

Related U.S. Application Data

(60) Provisional application No. 62/441,265, filed on Dec. 31, 2016.

(51) Int. Cl.
*A61N 5/10* (2006.01)
*A61K 31/713* (2006.01)
(Continued)

(52) U.S. Cl.
CPC .......... *A61N 5/1038* (2013.01); *A61K 31/713* (2013.01); *A61K 41/17* (2020.01);
(Continued)

(58) Field of Classification Search
CPC ...... A61N 5/10–1084; A61N 2005/1085–1098
See application file for complete search history.

(56) References Cited

U.S. PATENT DOCUMENTS 7,963,902 B2    6/2011  Blankenbecler
8,168,164 B2    5/2012  Low et al.
(Continued)

FOREIGN PATENT DOCUMENTS

WO    2016102735 A1    6/2016

OTHER PUBLICATIONS

International Preliminary Report on Patentability, dated Mar. 26, 2019.
(Continued)

*Primary Examiner* — Thaddeus B Cox
(74) *Attorney, Agent, or Firm* — Cittone Demers & Arneri LLP; Henry J. Cittone

(57) ABSTRACT

A method of preventing damage to non-neoplastic, e.g. healthy cells, by irradiating the non-neoplastic cells with a low-dose radiation is provided. The method initiates a protective cellular response which prevents later damage to non-neoplastic cells by radiotherapy and an immune response against neoplastic cells. The method of preventing damage to non-neoplastic cells is provided where the low-dose radiation is interspersed with a high dose sessions which themselves are varied through the weekly schedule.

15 Claims, 2 Drawing Sheets

(51) Int. Cl.
  *A61N 1/30* (2006.01)
  *C07K 16/30* (2006.01)
  *A61K 41/17* (2020.01)

(52) U.S. Cl.
  CPC .............. *A61N 1/30* (2013.01); *A61N 5/1031* (2013.01); *C07K 16/30* (2013.01)

(56) References Cited

U.S. PATENT DOCUMENTS

| | | |
|---|---|---|
| 9,132,281 B2 | 9/2015 | Zeng et al. |
| 2002/0048588 A1 | 4/2002 | Madiyalkan et al. |
| 2006/0056589 A1 | 3/2006 | Engleward |
| 2009/0114846 A1 | 5/2009 | Blankenbecler |
| 2013/0251634 A1 | 9/2013 | Grdina |

OTHER PUBLICATIONS

International Search Report, dated Apr. 6, 2018.
Written Opinion of the International Searching Authority, dated Apr. 6, 2018.
Liu, S, "Cancer control related to stimulation of immunity by low-dose radiation", Dose Response, Aug. 28, 2006, vol. 5, No. 1, pp. 39-47.
Kaur et al., "Radiation-induced effects and the immune system in cancer" Front Oncol, Dec. 17, 2012, vol. 2, Article 191, pp. 1-10.
Bonner, W. "Low-dose radiation: Thresholds, bystander effects, and adaptive responses," PNAS, Apr. 18, 2003, vol. 100, No. 9, pp. 4973-4975.
Janiak et al. "Cancer immunotherapy: how low-level ionizing radiation can play a key role," Cancer Immunol Immunother, Mar. 20, 2017, vol. 66, Iss. 7, pp. 819-832.
Han et al. "Radiation-Guided Gene Therapy of Cancer", Technology in Cancer Research and Treatment, Aug. 31, 2006, vol. 5, No. 4, pp. 457-444.
Tang et al. "Low-dose or low-dose-rate ionizing radiation-induced bioeffects in animal models," Journal of Radiation Research, Dec. 27, 2016, vol. 58, Iss. 2, pp. 165-182.
Park et al., "The Effect of Radiation on the Immune Response to Cancers," International Journal of Molecular Sciences, Jan. 10, 2014, vol. 15, No. 1, pp. 927-943.
Blankenbecler, "Low-dose Pretreatment for Radiation Therapy", International Dose-Response Society, Sep. 10, 2010 (online), vol. 8, Iss 4, Oct. 1, 2010.
Blankenbecler, "Radiation Worker Protection by Exposure Scheduling," International Dose-Response Society, vol. 8, Iss. 4, Oct. 1, 2011.

REDUCING DAMAGE FROM RADIATION THERAPY AND INCREASING CANCER KILL RATES BY INTERWEAVING OF LOW AND HIGH DOSE SESSIONS

CROSS-REFERENCE TO RELATED APPLICATIONS

The present application is the U.S. National Stage of PCT International Patent Application No. PCT/US2018/012097, filed Jan. 2, 2018, which claims priority to and benefit of U.S. Provisional Patent Application No. 62/441,265, filed 31 Dec. 2016, the entire disclosures of each of which are considered part of the disclosure of this application and are hereby incorporated by reference in their entireties.

FIELD OF THE INVENTION

The present invention relates to the field of radiation therapy, and more particularly, to a process of using radiation therapy in treatment of neoplastic diseases, uncontrolled cell growth, cancer and the like.

BACKGROUND

Neoplastic diseases, commonly recognized as cancer, can be formed anywhere in the body part due to abnormal growth of the cells or when the cells do not respond normally to growth regulation signals. Consequently, some or all of their descendants may proliferate inappropriately to produce tumors. Neoplasms that invade surrounding tissues and ultimately spread throughout the body are called malignant neoplasms or cancers. Several ways of treating neoplastic diseases have been developed over the years. The two main methods are radiation therapy and chemotherapy, and new methods are being developed such as immunotherapy. To reduce damage to the surrounding healthy cells, various schemes involving the radiation beam structure and the motion of the radiation source around the patient have been utilized. One of the schemes involves radioactive pellets placed inside the cancer itself, termed brachytherapy.

During the radiation therapy, the cancerous cells are exposed to a lethal dose of radiation, which kills and suspends the growth in cancerous cells thereby aiding in removing of neoplastic cells. However, the high dose radiation also effects the surrounding healthy tissues along with the cancerous cells. Various studies have been conducted to minimize the effects caused by high dose radiations on the surrounding healthy tissues.

Researchers have found that a low dose exposure of radiation to healthy cells surrounding the cancerous cells induce adaptive response in the healthy cells, which protects the healthy cells from subsequent exposure by high dose radiation during standard radiotherapy treatment. In this regard, a study showing the response of a cell exposure to low dose radiation and high dose radiation was conducted in "Comparison of low and high dose ionizing radiation using topological analysis of gene co-expression networks," BMC Genomics (2012) by Monika Ray, Reem Yunis, Xiucui Chen, and David M. Rocke, hereinafter referred to as Ray, et al. The experiment was conducted by exposing two different identical cells with a low dose radiation and a high dose radiation and the cells were observed at four time points after exposure to measure the changes in modulation of different gene sets compared to a control sample. It was found that the exposure of cells with low dose radiation resulted in modulation of genes responsible for immune response at three hours after exposure. At 8 hours post exposure, the gene set for metabolic processes and DNA damage, such as regulation of G1/S stage were expressed. At 24 hours post exposure, changes in gene sets responsible for WNT signaling, Mitotic phase checkpoints, NeK regulation in the cell cycle were observed. Similarly changes in gene modulation of cells exposed to high dose radiation were observed. At 3 hours post exposure, there is change in genes responsible for SCF complex, regulation of cell cycle, and regulation of G1/S transition. At 8 hours post exposure, regulation of G2/M and G1/S checkpoints and apoptosis occurs. At 24 hours post exposure, modulation of genes responsible for glutathione metabolism, mitotic phase checkpoints, mitosis phase processes, WNT signaling and NeK regulation in cell cycle was observed. From Ray et al, it was observed that exposure of a cell to a low dose of radiation modulates one or more genetic pathways responsible for cell repair proteins and immune response for a period of time post exposure and that this genetic response is markedly different from that produced by a high dose of radiation.

Researchers have also examined the effect of low dose exposure in order to reduce the harmful effects of high dose exposure in human cells. In this regard, see the review "Global Gene Expression Alterations as a Crucial Constituent of Human Cell Response to Low Doses of Ionizing Radiation Exposure", National Institutes of Health (2015) by Mykyta Sokolov and Ronald Neumann, hereinafter referred as Sokolov et al. discloses the modulation of cell repair genes in response to low dose exposure. Sokolov et al. discloses that low doses of ionizing radiation changes the gene expression in order to protect the human cells/tissues from harmful effects of challenging dose exposure. After being irradiated by a low-dose radiation, the cell initiates a repair sequence and many genes were modulated in the procedure. The genes that produce repair proteins were turned on; the relevant proteins were then produced for a period of time, known to be up to several days. For example, base excision repair (BER) genes and proteins in human BER pathway repairs radiation-induced single-strand breaks, base damage, and basic sites in both nuclear and mitochondrial DNA whereas non-homologous end joining (NHEJ) is involved in fixing DNA double stranded breaks (DSBs) in human cells. In a specific experiment, the peripheral blood mononuclear cells were purified and exposed to priming low dose radiation of 0.1 Gy. After 4 hours, the peripheral blood mononuclear cells were exposed to high dose radiation of 2.0 Gy. The corresponding expression profiles of aforementioned genes and proteins were examined for 30 minutes to 4 hours after the high dose. As a result of low and high dose radiation, the BER genes like APE1, FEN1, LIG1, MBD4 and OGG1 showed up-regulation at mRNA and protein levels in the primed cell. Similarly, NHEJ genes like XRCC5, XRCC6, NHEJ1 and LIG4 were overexpressed at four hours post-irradiation both at the transcript and protein levels. Such kind of overexpression in some BER and NHEJ genes and proteins underlies the active involvement of both BER and NHEJ pathways in human Radio Adaptive Response (RAR). During the procedure followed by other doses, the low dose radiation exposure evoked cellular alert responses to protect against subsequent high dose radiation damage, wherein RAR provided the cellular repair processes.

Similarly, gene expression profiles of DNA Damage Responsive (DDR) genes after low dose radiation exposure and high dose radiation exposure were studied at 1 and 5 hours post irradiation. The level of expression of ATM, ATR, GADD45A, CDKN1A, TP53, CDK2, HDM2, and CCNE was studied using RT-qPCR. The data showed a significant dose-dependent induction of CDKN1A and GADD45A genes up to 1 Gy at 5 hours post irradiation. RAR was observed only with TP53, CDK2, and CCNE.

The aforementioned study and experiment conducted by Sokolov et. al. disclosed that a properly chosen low-dose radiation applied to a cell, modulates its repair genes. Some were turned on to produce proteins that affect the repair. Other genes were turned off. This latter action can conserve energy needed for the repair, and can also increase the time to the next scheduled mitosis (cell division). This gives more time to affect repairs before the errors can be passed onto the next generation.

Another study in "A History of the United States Department of Energy (DOE) Low Dose Radiation Research Program: 1998-2008" by Dr. Antone L. Brooks, shows that irradiation changes the gene expression in many genes and gene expression was altered as a function of radiation dose, with identified low dose and high dose genes. The aforementioned studies show the modulation of genetic pathway by low dose radiation in the one or more non-neoplastic cell.

Utilizing the above analysis, various methods have been proposed in prior art to generate adaptive response in the healthy cells using low dose radiation before the subsequent exposure to high dose radiation. U.S. Pat. No. 7,963,902 discloses a method that utilizes the adaptive response generated by a low dose radiation in the healthy cells. In this method, the non-neoplastic cells surrounding the cancerous cells are exposed to a low dose radiation that induces metabolic pathways in the healthy cells that increases the probability of survival of the healthy tissues upon various insults such as subsequent radiation therapy. The pre-dose of healthy cells with radiation inures a much higher probability of their long term survival, and thereby reduces the adverse events associated with radiation therapy.

The method disclosed in U.S. Pat. No. 7,963,902 does not utilize other benefits associated with low dose radiation exposure apart from the adaptive response in healthy cells and, therefore, additional improvements in the protocols and extensions to utilize the benefits of low dose radiations are needed. Studies have also been conducted to examine other effects of low dose radiation on healthy and cancerous cells. In this regard, studied conducted by Ross in "Consensus of the effect of X-rays on bacterias", Hygie Vol. 56, pp 341-344, (1909) first showed that mice treated with low-level radiation were more resistant against bacterial disease. This has been explained by immune response induced by the low dose of radiation. E. J. Broome, D. L. Brown and R. E. J. Mitchel, International Journal of Radiation Biology. 75, 681-690 (1999), have found that low doses of in-vivo beta radiation of mouse skin 24 hour prior to the application of a DNA damaging carcinogen reduced tumor frequency by approximately 5 fold. The low radiation dose activates the repair of DNA breaks. This group has also shown that an adaptive response to low doses of LET radiation occurs in all organisms thus far examined, from single cell lower eukaryotes to mammals. These responses reduce the deleterious consequences of DNA damaging events, including radiation-induced or spontaneous cancer and non-cancer diseases in mice.

The immune response can be used as an effective weapon against cancer. To do so they need to leave the bloodstream and reach the tumor, but changes in its surroundings often prevent them from doing so. In the study conducted at the German Cancer Research Center (Deutsches Krebsforschungszentrum, DKFZ), "Radiation therapy mobilizes the immune system against tumors", by Kas/Sel, it is discovered that local applications of low doses of radiation helps immune cells to escape blood vessels and enter tumor tissue in all mammals tested. However, there is no therapy heretofore known which provides for the creation of an adaptive response in healthy tissue that is antagonistic to cancer cells in said healthy tissue or nearby cancer tissue.

Thus, there is a need for an approach that utilizes adaptive response in the surrounding healthy cells and sensitive organs and immune response of the body to treat cancer cells. In order to solve the aforesaid problems, the present invention solves the problem by providing a method that not only elicits repair mechanism in healthy tissue but also generates an immune response in both cancerous and nearby cancerous tissues prior to high dose radiation to reduce the inadvertent damage to the healthy cells and the sensitive organs, as well as increase the cancer cell kill rate by applying an interweaving low dose of radiation to non-neoplastic and neoplastic cells in conjunction with high dose radiation.

SUMMARY OF INVENTION

The prior art teaches against applying low dose radiation to cancer cells. The present invention advances prior art by eliciting an immediate immune response in the neoplastic cells that outweighs the cellular repair response in neoplastic cells. The low dose radiation neoplastic cellular response is counter-intuitive to prior art. Counter to all previous studies, low dose radiation on the cancer cells has been shown to increase cancer kill rates to as high as 5 fold.

The present invention addresses the need in the art by providing a method for protecting normal healthy cells from radiation therapy and generating an immune response against tumor cells. Once so protected, a patient may receive radiation therapy and experience a reduction or elimination of adverse events such as damage to organs and tissues, follow-on cancers, movement of cancerous cells into adjacent healthy cells, shortened lifespan and considerable patient discomfort.

In a first aspect of the present invention, a method of killing cancerous cells is provided. The method comprising: (a) administering a low dose radiation to neoplastic tissues and non-neoplastic cells surrounding neoplastic cells; wherein said low dose radiation elicits repair mechanism in the non-neoplastic cells and elicits antibodies against neoplastic tissues; and wherein said low dose radiation on neoplastic tissues causes anchors to form in the blood vessels within said neoplastic tissues that aids in latching of antibodies to anchors, allowing the antibodies to enter nearby neoplastic cells and kill them; waiting for a period of 48 to 72 hours and administering a high dose radiation to said neoplastic tissues. Irradiating the non-neoplastic cells modulates one or more genetic pathway responsible for cell repair proteins and an immune response in the body against neoplastic tissues. The immune response against the tumor or neoplastic cells remain active for a period of 48 hours to 72 hours, during which the antibodies present against the neoplastic tissues exit from the blood stream and latch on to the anchors present on the neoplastic cells. These anchors are formed on the neoplastic cells by exposure to low dose radiation on the tumor cells. The low dose radiation administered to the neoplastic cells is in range of 5 cGy to 20 cGy. The non-neoplastic cells exposed to the low dose radiation are in close proximity to the neoplastic cells (0.1 cm to 3 cm). The method can be used as a method of therapeutic treatment of cancer with radiotherapy.

In a second aspect of the present invention, a method for killing cancerous cells is provided. The method comprising: (a) targeting a tumor tissue and one or more non-neoplastic cells present in vicinity of a tumor tissue with a predetermined low dose of radiation, wherein said low dose radiation induces a cellular repair process in said one or more non-neoplastic cell and immune response against tumor tissues; and wherein the low dose radiation on the tumor tissue causes anchors to form in the blood vessels within said tumor tissue that aids in latching of antibodies to anchors, allowing the antibodies to enter nearby tumor cells and kill the tumor cells; (b) waiting for a period of 48 to 72 hours and irradiating the tumor tissue with a high dose radiation; and wherein the above steps are repeated till the recommended dose of high radiation is completed. The one or more anchors created on the tumor tissues are the result of exposure of tumor tissues to a low dose radiation. The antibodies will bind to the anchors and destroy the cancer cells. This prevents the spread of tumor tissues to surrounding healthy cells during the course of treatment. The low dose radiation applied to the tumor tissues and the non-neoplastic cells is in the range of 5 cGy to 20 cGy. The low dose radiation also modulates genetic pathway in healthy tissues to generate repair proteins which prevents the harmful effects of subsequent high dose radiation. The immune response thus initiated by the low dose radiation inhibits the proliferation of neoplastic cells and movement of neoplastic cells to adjoining healthy tissues during the course of treatment.

In a third aspect of the present invention, a method for killing cancerous cells is provided. The method comprising: (a) administering a low dose radiation to neoplastic tissues and non-neoplastic cells surrounding neoplastic tissues; wherein said low dose radiation elicits antibodies against neoplastic tissues and elicits a repair mechanism in the non-neoplastic cells; and wherein said low dose radiation on neoplastic tissues causes anchors to form in the blood vessels within said neoplastic tissues that aids in latching of antibodies to anchors, allowing the antibodies to enter nearby neoplastic cells and kill them; (b) waiting for a period of 48 to 72 hours and administering a second predetermined low dose radiation to the non-neoplastic cells surrounding neoplastic tissues, wherein said second predetermined low dose radiation elicits repair mechanism in said non-neoplastic cells; (c) waiting for a period of 24 hours and administering a high dose radiation to act upon said remaining neoplastic tissues. The low dose radiation applied is in range of 5 cGy to 15 cGy and low dose radiation modulates the genes responsible for repair mechanism in the non-neoplastic cells. The antibodies created against neoplastic tissue prevents invading neoplastic cells from entering into non-neoplastic cells. Also, the repair mechanism induced in the non-neoplastic cells protects the cells from the high dose radiation.

It is possible to combine the new protocol that utilizes the immune response with the prior art as described in patent U.S. Pat. No. 7,963,902 (the content of which is herein incorporated by reference in its entirety) to achieve a more effective treatment. Three example protocols that make use of the repair and immune response are the following: In the prior art, the proposed protocol was a low dose irradiation of the surrounding healthy cells followed by about 24 hours later with the standard high dose treatment of the cancer cells which may be repeated over several days. This protocol is changed by applying a low dose to both the healthy and cancer cells and then 24-48 hours later applying the standard high dose treatment. A third protocol is to apply a low dose to both the healthy and cancer cells, wait for around 24-48 hours, apply the low dose to the healthy cells and then after 24 hours start the high dose standard treatment. Other similar sequences are possible.

DETAILED DESCRIPTION OF THE INVENTION

Figure 1:
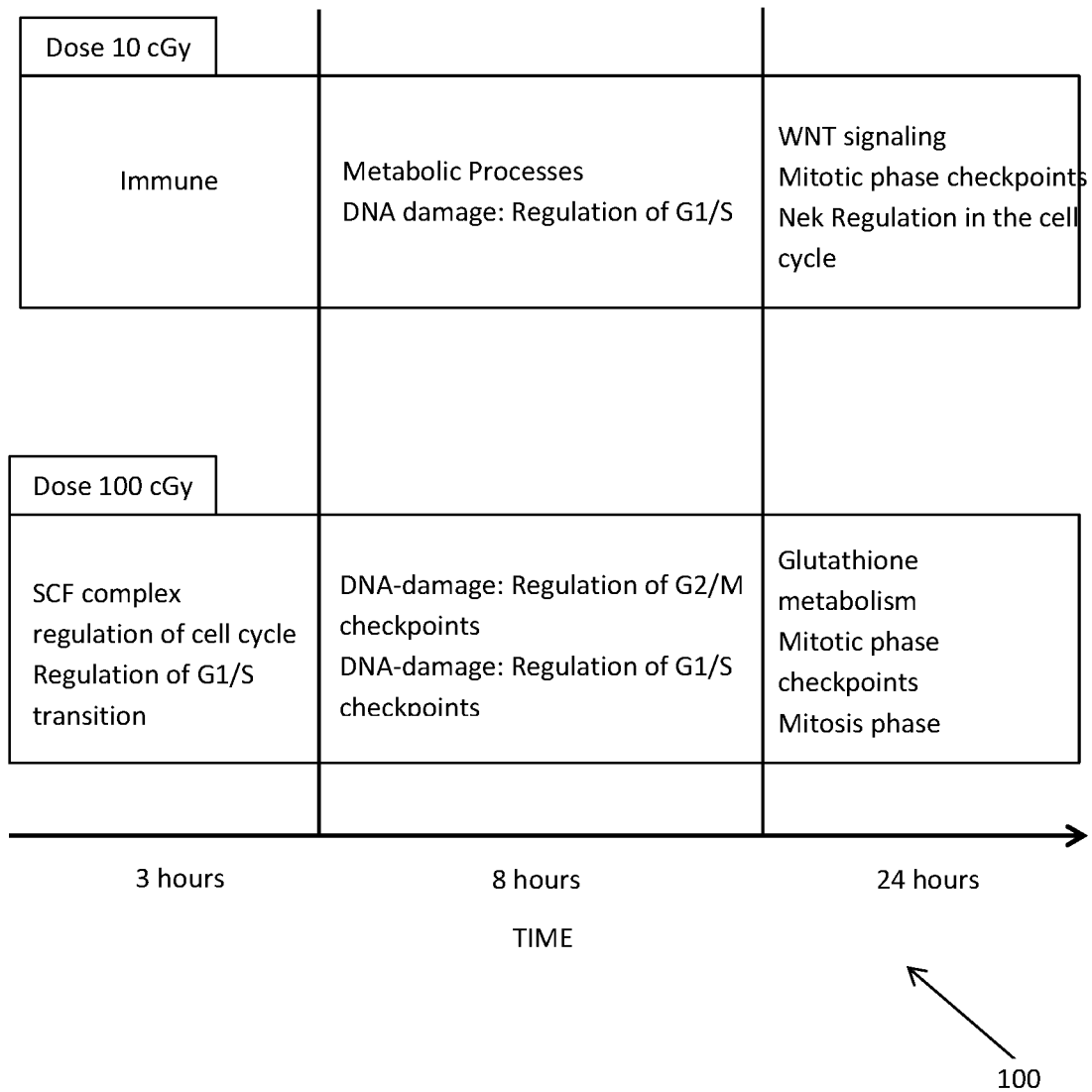
FIG. 1 is a table of the effects of radiation dosages in accordance with an embodiment of the present invention.
Figure 2:
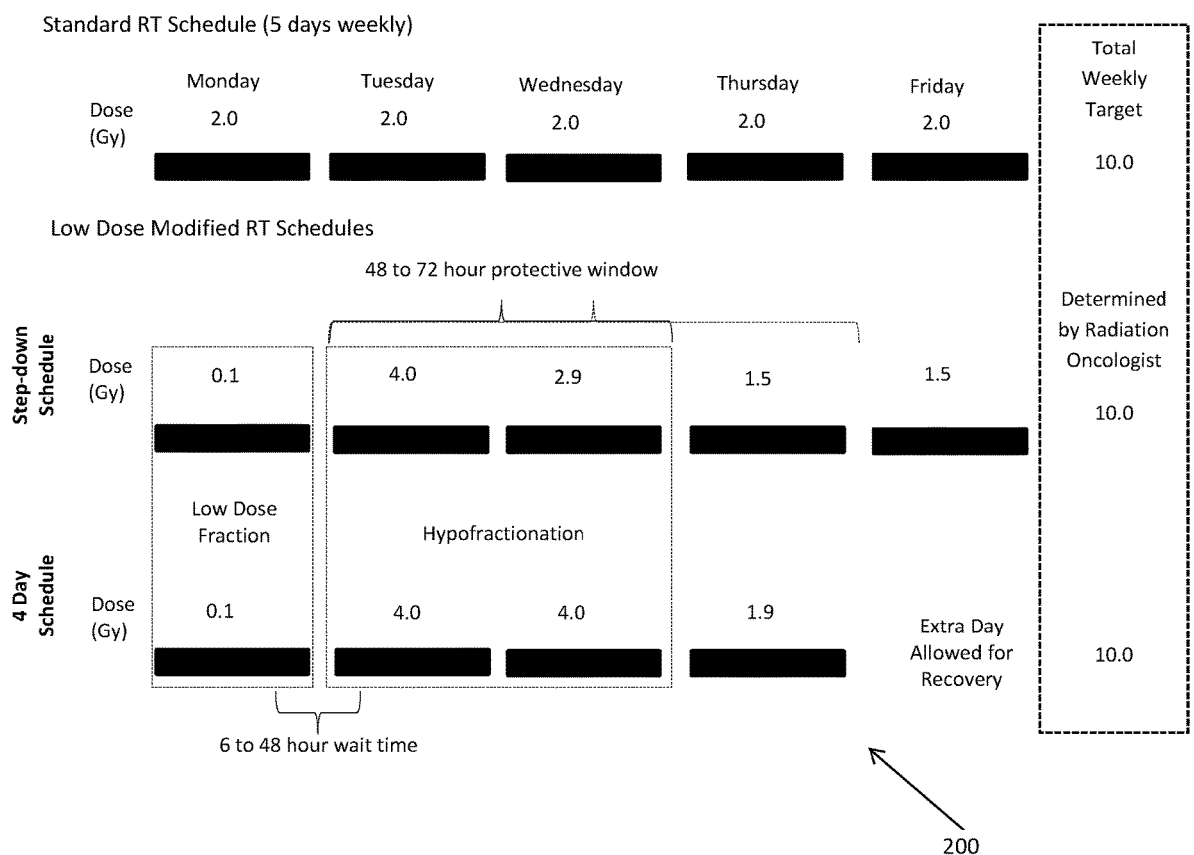
FIG. 2 is a time graph of a treatment regimen in accordance with an embodiment of the present invention.

In the following detailed description of embodiments of the invention, numerous specific details are set forth in order to provide a thorough understanding of the embodiments of the invention. However, it will be obvious to a person skilled in the art that the embodiments of the invention may be practiced with or without these specific details. In other instances, well known methods, procedures and components have not been described in details so as not to unnecessarily obscure aspects of the embodiments of the invention.

Furthermore, it will be clear that the invention is not limited to these embodiments only. Numerous modifications, changes, variations, substitutions and equivalents will be apparent to those skilled in the art, without parting from the spirit and scope of the invention.

As used herein, the terms neoplastic (all of its forms), cancer (all of its forms), and tumor (all of its forms) are used interchangeably to indicate a cell, tissue, or condition in which there is uncontrolled or abnormally fast growth of one or more cells of a particular type. Such growth can happen in vivo to produce a mass of cells within an organism, such as a human, or can occur in vitro to produce a culture of cells that might or might not have characteristics of cell lines. Accordingly, such cells or tissues can be, but are not necessarily, immortal. Likewise, the cells or tissues can be, but are not necessarily, primary cells obtained directly from a cancerous tissue.

Furthermore, as used herein, the terms radiation (and all of its forms) and electromagnetic energy are used interchangeably to indicate energy of one or more wavelengths of the electromagnetic spectrum. The invention is not limited to the use of particular wavelength, but instead can be used with any wavelength of the electromagnetic spectrum. For example, the invention contemplates use of a particular wavelength of energy that can activate a substance that can absorb one wavelength of energy and re-emit at another wavelength. For ease of reference, electromagnetic energy is typically referred to herein as radiation, and this term can be broadly interpreted.

More specifically, radiation is energy that comes from a source and travels through some material or through space. Thus, light, heat, and sound are types of radiation. One useful type of radiation according to the present invention is ionizing radiation, which is radiation that can produce charged particles (i.e., ions) in matter. Ionizing radiation is often produced in the medical setting by man-made devices, such as CT Scan, X-ray, or Linear Accelerator Machines (LINAC). It is well known that ionizing radiation can be produced by unstable atoms (i.e., radioactive atoms), which are atoms that have an excess of energy, mass, or both, and which shed or emit that energy and/or mass in the form of radiation in order to achieve a stable state. For the purposes of this invention, it is to be understood that there are two kinds of radiation: electromagnetic (e.g., light, gamma radiation, X-rays) and particulate (e.g., proton or neutron emission, beta and alpha radiation).

It is also to be understood that, where the invention relates to therapeutic treatment of a subject, a diagnosis of a localized cancer has been made and the size, shape, and location of the cancerous mass has been determined by standard methods known in the art. In other words, it is to be understood that the invention relates to in vivo therapy of a patient in need thereof, and the routine procedures for identifying such patients and characterizing their tumor(s) have been performed. By subject, it is meant any living organism in which a neoplasia may exist. Thus, a subject may be, but is not limited to, a human or other animal (e.g., a dog, cat, horse, bird, or other companion or agricultural animal). As used herein, the terms subject, patient, person, and animal, unless otherwise indicated, are used interchangeably to indicate a living organism in which a neoplasia may exist. Accordingly, the present invention has applications in both the human health field and in veterinary medicine.

The present invention discloses a method for protecting normal healthy cells from radiation therapy by inducing protecting mechanism in healthy cells and eliciting an immune response in the body; and utilizing the protecting mechanism and immune system to design radiation dosage schedule. After protecting the normal healthy cells through low dose radiation, a patient may receive radiation therapy for the treatment of neo-plastic diseases and experience a reduction or elimination of adverse events and discomfort such as damage to healthy organs and tissues, follow-on cancers, shortened lifespan and the like. In addition, the immune response initiated by the low dose radiation helps in killing tumor cells and prevents the spread of tumor cells to surrounding healthy cells during the course of radiation therapy treatment.

As a general matter, the method relates to pre-treating the tumor tissues and healthy cells, including those surrounding the neoplastic growth, with a low-dose of radiation. This low dose radiation exposure results in an adaptive response in healthy cells that increases the probability of survival of the healthy tissue upon various insults such as subsequent radiation therapy. During the subsequent radiation treatment of the tumor with a suitable protocol chosen to kill the cancerous cells, the surrounding healthy cells will inevitably be damaged as well. The pre-dose of the healthy cells with low dose radiation insures a much higher probability of their long term survival, and thereby reduces the adverse events associated with radiation therapy. The neoplastic tissues are also exposed to low dose radiation, which initiates an immune response against the cancerous cells by causing anchors to form in the blood vessels within said cancerous cells. The antibodies latches to the anchors and thus allows the antibodies to enter nearby cancerous cells and kill them. The pre-dose of the neoplastic cells with low dose radiation increases the cancer kill rate by up to 5 fold.

The effect of radiation on a cell depends strongly on the type of cell and the amount of radiation and its dose rate. Once irradiated by a low-dose of radiation, a cell initiates a repair sequence. Many genes are modulated in the procedure. The genes that produce repair proteins are turned on; the relevant proteins are then produced for a period of time, known to be up to several days. As these proteins are produced and move throughout the cell, they start repairing the damage. Since this active repair period lasts for days, if the cell is then damaged again during this time, for example by radiation (i.e. radiotherapy) or a high dose of radiation, the repair commences immediately and at near full strength.

Under aspects of the present invention, time spacing of the radiotherapy sessions as well as the dose per session are chosen to increase the efficacy of the adaptive response in repairing radiation damage suffered by healthy cells. When a cell receives a high dose of radiation, genes are also modulated, but this gene set is very different from the ones that are modulated by a low dose. Since the cell response time also varies, under aspects of the present invention a mixed schedule of a low-dose of radiation interspersed with high radiation dose to both healthy and cancerous cell regions can be designed to increase the kill effectiveness of the cancerous cells and reduce or moderate the damage to the surrounding healthy cells.

In an embodiment, the present invention discloses the use of the time dependence of the adaptive response and immune response initiated by the low dose radiation, to improve the efficacy of radiation therapy. The cellular response and time scale of the response is different between a low dose and a high dose. Thus, by using this difference and interweaving the low and high dose sessions properly, an overall improvement in the therapy can be achieved.

The low dose radiation is applied to the neoplastic cells and healthy cells surrounding the tumor. Then after a selected wait period, a radiotherapy treatment is applied. Low dose radiation may be applied prior to multiple radiation treatments or prior to a series or a single radiation treatment. The healthy cells inevitably receive a radiation exposure during radiotherapy sessions but have the extra protection of the adaptive response initiated by the low dose radiation applied prior to the radiotherapy.

The invention relates to in vivo and in vitro treatment of cells. In aspects relating to in vivo uses, it is generally a method of therapeutic treatment, which can be curative or prophylactic. Thus, the method can be practiced on a subject suffering from a neoplastic disease, such as one in which a neoplastic mass is growing, to reduce the growth of, reduce the size of, or eliminate the neoplastic mass. In addition, the method can be practiced on a subject who previously suffered from a neoplastic disease, such as the one who had a neoplastic mass removed by surgery or radiation treatment, to ensure that all neoplastic cells of the mass are killed. The invention provides particular protocols for pre-dosing healthy cells and tissues with low dose radiation, while avoiding irradiating cancerous cells, in order to induce a cellular repair response in the healthy cells/tissues, followed by a standard radiotherapy protocol.

In an embodiment of the present invention, a method for treating at least one neoplastic cell with a harmful amount of electromagnetic energy is provided. The method involves the induction of adaptive response in healthy cells surrounding the tumor mass so that they may be able to withstand the harmful effects of subsequent high dose exposure of radiation. The method also involves initiating an immune response in the body. It has been found during the experiment that a low dose exposure to cancerous cells and healthy cells initiate an immune response in the body against cancerous cells.

The method for treating at least one neoplastic cell comprises: a) administering a low dose radiation to neoplastic tissues and non-neoplastic cells surrounding neoplastic cells within 0.1 to 3.0 cm of a tumor; wherein said low dose radiation elicits repair mechanism in the non-neoplastic cells and antibodies against neoplastic tissues; and wherein said low dose radiation on neoplastic tissues causes anchors to form in the blood vessels within said neoplastic tissues that aids in latching of antibodies to anchors, allowing the antibodies to enter nearby neoplastic cells and kill them; (b) waiting for a period of 48 to 72 hours and administering a high dose radiation to neoplastic tissues. During this time period, immune response induced in the patient body acts on the cancerous cells and also prevents establishment of neoplastic cells in adjacent healthy tissues. The time spacing between the radiotherapy exposure and the high dose radiation application is chosen to maximize the efficacy of the adaptive response in repairing damage suffered by healthy cells.

The low dose radiation on the healthy cells modulates repair protein genes in the cell to induce protective adaptive response in non-cancerous tissue. The method utilizes this protective adaptive response of cell for modifying the radiation therapy dosage schedule. The pre-dose of the healthy cells with low dose radiation insures a much higher probability of their long term survival, and thereby reduces the adverse events associated with radiation therapy. The effect of radiation on a cell depends on the type of cell and the amount of radiation and its dose rate. For example, a muscle cell, a liver cell, and a breast cell, etc., react to radiation in different ways and the scale of the reaction depends on the radiation beam parameters. In choosing the specifics of the optimum low-dose radiation beam for treatment, these radiation beam parameters are chosen corresponding to the cell type being irradiated.

After pre-dosing a healthy cell with a low dose radiation, the cell responds by modulating genes that produce repair proteins that control certain cell functions, which include creating immune response among others. These proteins then proceed to repair the damage to the cell, a process that lasts for days. The low dose radiation induces metabolic changes in the non-neoplastic cells and modulates the repair protein genes responsible for cell repair mechanism. As these proteins are produced and moved throughout the cell, they start repairing the damage. The protein producing genes remain activated for a period of time, up to several days; therefore the relevant protein is being produced and keeps on repairing the damaged cells for that time period. Since, the active repair period lasts for days, if the cell is then damaged again during this time, for example by standard high-dose radiotherapy, the repair commences immediately and at near full strength.

Exposure with low dose of radiation also turns off other genes; this action conserves energy needed for the repair and also increases the time to the next scheduled mitosis (cell division). This gives more time to affect repairs before the errors can be passed on to the next generation.

Table 1 represents some of the genes that are known to respond to the low dose radiation:

TABLE 1

| Group | Number of Genes | Responsive Genes | Function |
| --- | --- | --- | --- |
| I | 11 | MBD4, OGG1 | Base excision repair (BER) |
| II | 6 | APEX1, LIG3, PNKP | Other BER and strand break joining factors |
| III | 3 | PARP1, PARP2 | Poly(ADP-ribose) polymerase (PARP) enzymes |
| IV | 3 | MGMT | Direct reversal of damage |
| V | 2 | TDP1 | Repair of DNA-topoisomerase crosslinks |
| VI | 10 | MSH2 | Mismatch excision repair (MMR) |
| VII | 24 | XPC, DDB2, LIG1 | Nucleotide excision repair (NER) |

The exposure of low dose radiation on neoplastic cells or tumor cells have effects, such as initiation of immune response in the body. The immune system usually recognizes cancer cells and "killer T cells" that invade the tumor tissues. Normally immune cells migrate into tissues through "anchors" formed by blood vessels. As the invading immune cells flow through blood stream, they latch onto the anchors and can thus leave the bloodstream. The problem with tumors is that they often prevent the anchors from forming, which prevents the killer T cells from using these exit points. The exposure of cancerous cell to low dose radiation leads to the formation of anchor molecules in the vessel wall. Additionally, the low dose exposure to healthy cells and cancerous cells results in generation of antibodies against tumor cells that lasts for several days. A low dose of radiation, striking as far away as 1.5 cm from the surface of a tumor, will excite an immune response not only in healthy tissues but also in nearby tumor cells. Due to the excitation of immune response, the growth of these tumor cells is then reduced. The immune response generated by the low dose radiation has an additional benefit, in that it prevents the cells from the tumor mass to invade the surrounding healthy tissues.

The main pathways of the immune response triggered by the low dose radiation includes, but are not limited to: a) Altered T cells and B Cell Signaling; b) Antigen presentation pathway; c) B cell development; d) OX40 Signaling Pathway. These pathways result in the production of molecules associated with Dendritic cell maturation, NF-kB signaling, and Fcγ receptor-mediated Phagocytosis in macrophages and monocytes.

It was found that this immune response is active within 24 hours of the exposure, whereas a natural trigger normally requires 6-8 days to become fully active. This quick response could be a very important feature in the application of low dose radiation. The low dose turns on the natural immune response as well as the induced adaptive response.

In an embodiment, the low dose radiation irradiated to non-neoplastic cell present in the vicinity is in the range of 5 cGy to 20 cGy, preferably between 8 cGy to 15 cGy.

In an embodiment, the low dose is administered by a neutron beam as well as by a standard X-ray/gamma beam.

After the exposure of low dose radiation on to the tumor cells and healthy cells, the immune system as well as adaptive repair systems becomes activated. There will be a waiting period of 48 to 72 hours, during which both systems act on the healthy cells and tumor cells. After the wait period of 48 to 72 hours, the neoplastic cells of tumor are irradiated with a high dose radiation in order to kill the tumorous or cancerous cells.

In an embodiment, the high dose radiation is given after a wait window, which is of duration 48 to 72 hours from the time of low dose radiation.

The weekly dosage schedule of radiation therapy is defined as standard schedule for different types of tumor and per day dosage is decided by dividing equally the weekly dosage in days. Since the repair period of non-neoplastic cells present in the vicinity of tumor cells remains active for few days of irradiation with low dose radiation, this active period can be used to irradiate the neoplastic cells with a substantially higher dose than the standard day dose. During this substantially high dose radiation, the non-neoplastic cells survive because of the induced protective property actuated by the predetermined low dose radiation.

Once the protective window of the non-neoplastic cell is over, the remaining dose level is divided between remaining days. Since, in the protective window, substantially higher doses of radiation have already been given, the remaining dosage level will therefore be much less, which can be given in a day or two.

In an embodiment, the strength of the high dose radiation in the protective window is larger than the strength of the high dose radiation after the protective window is closed. During the time window of the cell repairing process (protective window), if the non-neoplastic cell is being damaged again due to radiation (radiotherapy) or high dose radiation, then the repair commences immediately to heal the damaged cells.

EXAMPLE 1

In our most recent experimentation, human subjects with epithelial skin cells were treated in-vivo with two methodologies. The first patient received an interweaving low dose radiation of 10 cGY, specifically to the healthy tissue surrounding the localized skin cancer. The second patient also received low dose radiation of 10 cGy to both the neoplastic cells and healthy cells adjacent to the tumor. Both patients underwent biopsies before treatment, 24 hours after the low dose treatment, and then one week later after standard high dose radiation therapy.

The protocols were tested in-vivo, with DNA analysis verifying the effect of low dose radiation: a) the excitement of a cellular repair adaptive and immune response in healthy tissue surrounding the neoplastic cells. b) the excitement of a cellular repair adaptive response in neoplastic cells that is outweighed by the immune response in the neoplastic cells that increases cancer kill rates up to 5 fold. To clarify, the low dose radiation elicits antibodies against neoplastic tissues and elicits repair mechanisms in non-neoplastic cells and cells sensitive to radiation; and wherein said low dose radiation on neoplastic tissues causes anchors to form in the blood vessels within said neoplastic tissues that aids in latching of antibodies to anchors, allowing the antibodies to enter nearby neoplastic cells and kill them.

Scheduling of Low/High Dose Sessions

In an embodiment of the present invention, a method for interweaving of the low dose sessions among the high dose treatments of the standard therapy is provided. Irradiation of low dose to non-neoplastic cells triggers an immune response and causes an adaptive response that turns on certain repair genes, which then produce a set of proteins that proceeds to repair damage to the cell. The production of these genes lasts for a limited time. The duration of the complete repair process depends upon several factors, two of which are (1) the lifetime of the proteins themselves as they make repairs, and then as the cell divides, (2) the division of the proteins among the daughter cells. There is some evidence that the gene modulation lasts for at least 2 cell cycles. Consideration of these factors will lead to the optimum interweaving of the low and high dose sessions to optimize the survival of the healthy cells.

The method of interweaving low dose session among the high dose treatments of the standard therapy involves targeting one or more non-neoplastic cells in the vicinity of a tumorous tissue by irradiating with a predetermined low dose radiation, in order to induce the cell repairing process. After that the neoplastic cells (tumor tissues) are irradiated by high dose radiation for completing the standard weekly dose schedule. Since the adaptive response generated by low dose radiation lasts for a particular duration, the non-neoplastic cells in the vicinity of tumor cells are again irradiated with a low dose radiation to activate the cell repair genes. The second predetermined low dose is being scheduled for different time sessions based on the response of the various cell types because the radiation effect on a cell depends on its type, the exposed amount of the radiation, and the dose rate.

It is known that each cell type has its own characteristic lifetime. Therefore, since the optimum time between low dose exposures will depend upon cell lifetime, the dose schedule will depend upon the location of the cancerous cells, and the type of surrounding healthy cells. For example, typical times for cell renewal are: stomach 2-9 days, lung alveoli 8 days, skin epidermis 10-30 days, red blood cells 4 months, and liver hepatocyte cells 6 months. Therefore, in embodiments the low-dose radiation is scheduled to repeat after expiration of the cell renewal window and prior to the next radiotherapy treatment.

Each of the repair genes can initiate a complicated pathway that involves the excitation of many other subsequent genes. A study of these pathways is very important in the development of chemotherapy and other drug agents. The use of LDR to excite these pathways has many advantages over chemical excitation.

Also, the scale of the cell reaction depends upon the radiation beam parameters. So, while choosing the specification of the low dose radiation beam for treatment, the radiation beam parameters are chosen according to the type of the cell being irradiated.

The present invention utilizes induced protective adaptive response and immune response initiated by the low dose radiation to schedule radiation sessions in order to address the deficiencies and increase the benefits of the radiation therapy. The present invention provides a method for inducing protective adaptive response in the non-neoplastic cells that can further reduce the damage from radiation therapy by interweaving of low and high dose sessions. The method uses a predetermined low dose radiation to target the non-neoplastic cells to induce persistence power of the non-neoplastic cells, and neoplastic cells to induce immune response in the body. After increasing the persistence power of the neo-plastic cells, the method targets the cancerous cells by irradiating various predetermined level of high dose radiation for different predetermined period of time to kill the cancerous cells.

The method provided in the present invention utilizes a predetermined low dose of radiation to target non-neoplastic cells localized in the vicinity of the tumor cells in order to induce protective adaptive response in the non-neoplastic cells that increases the probability of survival of the healthy tissues from harmful radiations. The exposure of the predetermined low dose radiation on the non-neoplastic cells causes modulation of genetic pathways to develop cell repair proteins, that is further used to determine reaction of a pharmaceutical or chemical agents on the non-neoplastic cells. In an exemplary embodiment, the predetermined low dose radiation is in the range of 5 cGy to 15 cGy. Furthermore, the low dose radiation either can be administered by particulate radiation such as proton or neutron emission, beta and alpha radiation or by electromagnetic radiation such as light, radio waves, gamma rays, and X-rays.

The application of low dose radiation excites an immune response in the body. The irradiation of healthy body cells may induce DNA damage in the cell which alerts the immune system by signals displayed on the cell surface. This effect has a strong link to the innate immune system and tumor surveillance. The activation of the immune response is an important tool in the study of the effects of low dose radiation and its effects on cancer. It is known that the immune response will combat local inflammation and also retard the growth of the cancer. Due to induction of immune response by the low dose radiation, the adaptive response in whole body is produced and adverse effect of subsequent treatment with the high dose radiation on the healthy cells and tissues is prevented.

In another embodiment of the present invention, the method of killing cancerous cells comprises of: (a) administering a low dose radiation to neoplastic tissues and non-neoplastic cells surrounding neoplastic cells and cells sensitive to high dose radiation; wherein said low dose radiation elicits antibodies against neoplastic tissues and elicits a repair mechanism in the non-neoplastic cells and in non-neoplastic cells sensitive to the high dose radiation; and wherein said low dose radiation on neoplastic tissues causes anchors to form in the blood vessels within said neoplastic tissues that aids in latching of antibodies to anchors, on to said neoplastic tissues resulting in killing of said neoplastic cells; (b) waiting for a period of 48 to 72 hours allows the high dose radiation to act more effectively on the neoplastic tissues.

In other embodiments, the application of low dose radiation can also be used to excite an immediate immune response in the body, more quickly and efficiently than the body's typical immune response to cancer cells. The irradiation of healthy body cells induces DNA damage in the cell which alerts the immune system by signals displayed on the cell surface. This effect has a strong link to the innate immune system and tumor surveillance. The activation of the immune response is an important tool in the study of the effects of low dose radiation and its effect on cancer. The immune response will combat local inflammation and also retard the growth of the cancer by attacking cancer cells located near or in the irradiated tissues as well as throughout the body. Due to induction of the immune response by the low dose radiation, an adaptive response throughout the entire body is produced and adverse effect of subsequent treatment with the high dose radiation on the healthy cells and tissues is prevented.

In addition, the method includes irradiating the tumor tissues with one or more predetermined level of high dose radiation in order to kill the cancerous cells. During the high dose of the radiation, the non-neoplastic cells survive because of the induced protective property actuated by the predetermined low dose of radiation, and in this way the method minimizes the adverse effects of the radiation therapy. In an exemplary embodiment, the first predetermined time period of the high dose radiation is between 24 hours to 72 hours from the protective low dose radiation to optimize cancer kill rates, while sparing the patient from the lethal effects of high dose radiation on healthy tissues or cells.

During this time period, immune response induced in the patient body acts on the cancerous cells and also prevents establishment of neoplastic cells in adjacent healthy tissues. The time spacing between the radiotherapy exposure and high dose radiation is chosen to maximize the efficacy of the adaptive response in repairing damage suffered by healthy cells.

In another embodiment, the method of present invention can be used in similar possible sequences. For instance, the method comprises administering low dose radiation to health cells (non-neoplastic cells) that are adjacent to tumor tissue and to the neoplastic tissue. The low dose radiation on healthy cells elicits adaptive protective response and on tumor tissues, it elicits an immune response. Then a wait period of 48 to 72 hours is observed, during which antibodies can act on the tumor tissue. Thereafter, a low dose radiation is again administered to the healthy non-neoplastic cells, so that the adaptive response in them is triggered. After a wait period of 24 hours, high dose radiation is administered upon remaining cancerous cells. The present invention envisions another possible schedules for interweaving low dose radiation on non-neoplastic cells and neoplastic cells with high dose radiations.

In the regard of the radiation therapy, the aforementioned features become additional approaches to the therapy, which can be used to discern mockery for example. To avoid redundancy, in the description below, we shall mention radiation therapy, while keeping in mind that the same elements are also used for induced protective adaptive response treatment procedure of radiation therapy and equivalent applications, such as radiation and occupational hazards.

It will be apparent to those skilled in the art that other embodiments of the invention will be apparent to those skilled in the art from consideration of the specification and practice of the invention. While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention. It is intended that the specification and examples be considered as exemplary, with the true scope and spirit of the invention being indicated by the claims.

I claim:

1. A method for killing cancerous cells comprising:
a. administering a first dose of radiation between 5 cGy to 20 cGy to neoplastic tissues and non-neoplastic cells surrounding neoplastic tissues;
wherein said first dose of radiation elicits a repair mechanism in the non-neoplastic cells and elicits antibodies against neoplastic tissues;
and wherein said first dose of radiation on neoplastic tissues causes anchors to form in one or more blood vessels within said neoplastic tissues that aids in latching of antibodies to anchors, allowing the antibodies to enter the neoplastic tissues to kill;
(b) waiting for a period of 48 to 72 hours and administering a second dose of radiation of 1 Gy or more than 1 Gy to said neoplastic tissues.

2. The method of claim 1, wherein irradiating the non-neoplastic cells with the first dose of radiation modulates one or more genetic pathways responsible for cell repair proteins.

3. The method of claim 2, wherein the modulation of one or more genetic pathways by the first dose of radiation on the non-neoplastic cells is used to determine reactivity of one or more pharmaceuticals or chemical agents on the non-neoplastic cells.

4. The method of claim 2, wherein the modulation of one or more genetic pathways by the first dose of radiation on the non-neoplastic cells is used to determine protection against radiation hazards.

5. The method of claim 1, wherein the non-neoplastic cells are in contact with or in close proximity to a target neoplastic cell of a neoplastic disease.

6. The method of claim 1, wherein the first dose is administered by a neutron beam or a standard x-ray or gamma beam.

7. The method of claim 1, wherein the non-neoplastic cells surrounding the neoplastic tissues are in a range of 0.1 cm to 3 cm of the neoplastic tissues.

8. A method for killing cancerous cells comprising:
(a) targeting a tumor tissue and one or more non-neoplastic cells present in a vicinity of a tumor tissue with a first dose of radiation between 5 cGy to 20 cGy, wherein said first dose of radiation induces a cellular repair process in said one or more non-neoplastic cells and an immune response against tumor tissues;
and wherein the first dose of radiation on the tumor tissue causes anchors to form in one or more blood vessels within said tumor tissue that aids in latching of antibodies to anchors, allowing the antibodies to enter the tumor tissue to kill;
(b) waiting for a period of 48 to 72 hours and irradiating the tumor tissue with a second dose of radiation of 1 Gy or more than 1 Gy; and
wherein the above steps are repeated until a predetermined radiation dosage is completed.

9. The method of claim 8, wherein the first dose of radiation modulates one or more genetic pathway of non-neoplastic cells to induce cell repair proteins.

10. The method of claim 8, wherein the immune response initiated by the first dose of radiation inhibits proliferation of neoplastic cells.

11. The method of claim 8, wherein the immune response protects the non-neoplastic cells from the second dose of radiation.

12. A method of killing cancerous cells comprising:
a. administering a first dose of radiation between 5 cGy to 20 cGy to neoplastic tissues and non-neoplastic cells surrounding neoplastic tissues;
wherein said first dose of radiation elicits antibodies against neoplastic tissues and elicits a repair mechanism in the non-neoplastic cells;
and wherein said first dose of radiation on neoplastic tissues causes anchors to form in one or more blood vessels within the neoplastic tissues that aids in latching of antibodies to anchors, allowing the antibodies to enter the neoplastic tissues to kill;
b. waiting for a period of 48 to 72 hours and administering a second predetermined dose of radiation between 5 cGy to 20 cGy to the non-neoplastic cells surrounding neoplastic tissues, wherein said second predetermined dose of radiation elicits a repair mechanism in said non-neoplastic cells;
c. waiting for 24 hours and administering a third dose of radiation of 1 Gy or more than 1 Gy to act upon the neoplastic tissues.

13. The method of claim 12, wherein the first dose of radiation modulates one or more genes responsible for the repair mechanism in the non-neoplastic cells.

14. The method of claim 12, wherein the repair mechanism in non-neoplastic cells protects the non-neoplastic cells from the dose of radiation.

15. The method of claim 12, wherein the non-neoplastic cells surrounding the neoplastic tissues are in a range of 0.1 cm to 3 cm of the neoplastic tissues.

\* \* \* \* \*